United States Patent [19]
Masterman et al.

[11] Patent Number: 6,058,541
[45] Date of Patent: May 9, 2000

[54] CRIMPED BRISTLE TOOTHBRUSH

[75] Inventors: Thomas Craig Masterman, Foster City, Calif.; Jeffrey Meessmann, Iowa City, Iowa; Jean Spencer, Boston, Mass.; Georges Driesen, Weilrod, Germany; Armin Schwarz-Hartmann, Albig, Germany; Peter Hilfinger, Bad Homburg, Germany

[73] Assignee: Gillette Canada Inc., Kirkland, Canada

[21] Appl. No.: 08/886,425

[22] Filed: Jul. 1, 1997

Related U.S. Application Data

[63] Continuation-in-part of application No. 08/675,096, Jul. 3, 1996, abandoned.

[51] Int. Cl.$^7$ .............................. A61C 17/22; A46B 9/04; A46B 9/06
[52] U.S. Cl. .............................. 15/28; 15/22.1; 15/167.1; 15/207.2; 15/DIG. 5
[58] Field of Search ............................... 15/167.1, 207.2, 15/DIG. 5, DIG. 6, 22.1, 28

[56] References Cited

U.S. PATENT DOCUMENTS

| | | | |
|---|---|---|---|
| 2,317,485 | 4/1943 | Rider | 15/167.1 |
| 2,790,986 | 5/1957 | Schwartz et al. | 15/207.2 X |
| 3,118,527 | 1/1964 | Lombardy et al. | 192/107 M |
| 3,295,156 | 1/1967 | Brant | 15/167.1 |
| 3,411,979 | 11/1968 | Lewis, Jr. | 15/207.2 X |
| 3,425,206 | 2/1969 | Holton | 57/208 |
| 3,505,163 | 4/1970 | Meers et al. | 428/371 |
| 3,567,569 | 3/1971 | Ono et al. | 15/207.2 X |
| 3,840,932 | 10/1974 | Balamuth et al. | 15/167.1 |
| 4,373,541 | 2/1983 | Nishioka | 15/207.2 X |
| 4,524,480 | 6/1985 | Bloom | 15/207.2 |
| 4,616,374 | 10/1986 | Novogrodsky | 15/167.1 |
| 5,161,555 | 11/1992 | Cansler et al. | 15/207.2 X |
| 5,195,546 | 3/1993 | Cansler et al. | 132/317 |
| 5,268,005 | 12/1993 | Suhonen | 15/167.1 X |
| 5,467,495 | 11/1995 | Boland et al. | 15/28 |
| 5,491,865 | 2/1996 | Gueret | 15/207.2 X |

FOREIGN PATENT DOCUMENTS

| | | | |
|---|---|---|---|
| 2757046 | 7/1979 | Germany | 15/207.2 |
| 3116189 | 12/1982 | Germany | 15/207.2 |
| 41 14 136 | 11/1992 | Germany . | |
| 94 08 268 U | 8/1994 | Germany . | |
| 295 01 338 | 8/1995 | Germany . | |
| 196 15 098 | 10/1997 | Germany . | |
| 15641 | 12/1897 | Switzerland | 15/DIG. 6 |
| 598821 | 2/1948 | United Kingdom | 15/207.2 |

OTHER PUBLICATIONS

International Organization for Standardization, International Standard ISO 8627:1987 (E), Ondontology "Stiffness of the Bristle Area of Toothbrushes," pp. 84–93.

Ullmann's Encyclopedia of Industrial Chemistry, Fibers, 6. Testing and Analysis, 2.6–2.6.2 "Crimp; Crimp Frequency; Crimp Ratio, Crimp Retention," A11:75–76.

Walczak, Formation of Synthetic Fibers, Practical Applications, 10–2b "Crimping," 310–311, 318 (1977).

*Primary Examiner*—Mark Spisich
*Attorney, Agent, or Firm*—Fish & Richardson P.C.

[57] ABSTRACT

An improved oral brush is provided that includes crimped bristles. The oral brush includes a body and, extending from the body, a plurality of crimped bristles. One such oral brush is an electric toothbrush, with a brush head having a preferred arrangement of tufts of crimped and straight bristles that are flexed by cyclic motions of the brush head toward and away from the tooth.

62 Claims, 13 Drawing Sheets

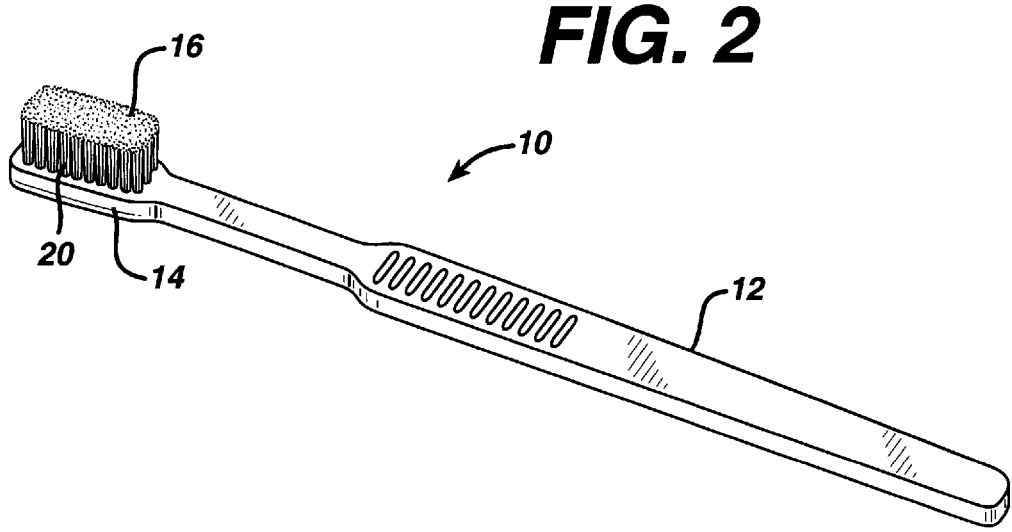
FIG. 2
FIG. 3
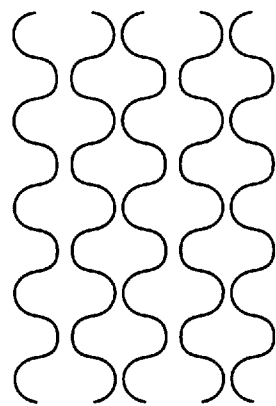
FIG. 3A
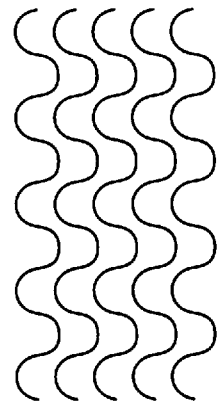

CRIMPED BRISTLE TOOTHBRUSH

CROSS REFERENCE TO RELATED APPLICATIONS

This application is a continuation-in-part of U.S. Ser. No. 08/675,096, filed Jul. 3, 1996 abandoned.

BACKGROUND OF THE INVENTION

The invention relates to toothbrushes and bristles for use in toothbrushes.

Most people suffer from tooth decay and/or gingivitis caused by plaque in the mouth. As a result, reducing the amount of plaque in the mouth has long been the target of persons working in the health care field. A common way of minimizing plaque is to brush the teeth regularly.

Toothbrushes are available having bristles with varying degrees of stiffness, commonly labelled "soft", "medium" and "hard". According to industry standards, such toothbrushes have stiffnesses, as measured by ISO 8627 (1987), of less than 7 centinewtons per square millimeter ($cN/mm^2$, soft), 6 to 9 $cN/mm^2$ (medium), and greater than 8 $cN/mm^2$ (hard). Soft brushes are comfortable to use, and minimize trauma and irritation of the gums. Typically, however, better cleaning is provided by stiffer, i.e., medium to hard, brushes.

SUMMARY OF THE INVENTION

The invention features an improved oral brush that includes crimped bristles. These crimped bristles are preferably formed by cutting crimped elongated filaments to a suitable length for use as bristles. The crimped bristles are low in stiffness, for a "soft" feel, but, unexpectedly, have been found to also provide excellent cleaning. By "crimped", it is meant that bristles have a plurality of deformations, e.g., bends, curves or protrusions, at intervals along their length. The term "crimp", as used herein, is intended to include what is referred to herein as "structural crimp", in which the ratio of the depth of the deformations (measured as twice the amplitude of the deformation minus the diameter of the bristle, where amplitude is defined as the distance from the longitudinal axis to the outermost surface of the bristle) to the diameter of the bristle is sufficiently great that the longitudinal centerline of the bristle is deformed and thus an imaginary longitudinal axis taken along the length of the bristle would not be parallel to the longitudinal centerline of the bristle (see FIG. 1B). The term "crimp" is also intended to include what is referred to herein as "surface crimp", in which the ratio of the depth of the deformation to the diameter of the bristle is sufficiently small so that the longitudinal centerline of the bristle is not deformed and thus the longitudinal centerline of the bristle is parallel to an imaginary longitudinal axis taken along the length of the bristle (see FIGS. 1C and 1D). The term "crimp" also includes combinations of structural and surface crimp occurring on a single bristle or different bristles.

The intervals between deformations may be regularly spaced, i.e., the crimp may be in the form of a sinusoidal or other regularly repeating wave-form of any desired shape (e.g., arcuate waves or angular waves), or the intervals may be irregular, i.e., the crimp may include randomly occurring deformations.

In one aspect the invention features an oral brush that includes a body and, extending from the body, a plurality of crimped bristles.

Preferably, the crimp lies in a single plane. It is also preferred that each bristle has substantially the same crimp geometry as each other bristle, e.g., each bristle has substantially the same shape crimp, and, if the crimp is sinusoidal or of similar non-random geometry, substantially the same frequency and amplitude. For example, the crimp of the bristles may be substantially sinusoidal, preferably having an amplitude of from about 0.01 mm to 1.0 mm, and a frequency of from about 0.5 to 50 crimps/cm, more preferably 0.5 to 8 crimps/cm. Structural crimp preferably has a width that is equal to the reciprocal of the frequency. Surface crimp preferably has a width of from about 0.05 to 2.0 mm, a ratio of depth of crimp to bristle diameter of from about 0.01 to 0.20, a deformation depth of from about 1 to 150 microns, and a total number of deformations per centimeter of from 1 to 50. The crimp of neighboring bristles may be in-phase, i.e., the waves of one bristle are in line with the waves of the bristles surrounding it, or may be out-of-phase, i.e., offset, either randomly or to a predetermined extent. Preferably, the bristles have a diameter of from about 0.003 inch to 0.020 inch. The bristles may have a stiffness of up to 9 centinewtons per square millimeter ($cN/mm^2$); preferred bristles have a stiffness corresponding to that possessed by conventional bristles used in standard "soft" or "extra soft" toothbrushes, i.e., a stiffness grade (according to ISO 8627) of from about 2 to 7 $cN/mm^2$.

In other preferred embodiments, the crimped filaments have a diameter of 0.006 inch and are mounted in tuft holes, each tuft hole preferably containing from 40 to 56 crimped filaments. It is also preferred that the non-crimped filaments be mounted along a perimeter of the body and said crimped bristles be mounted on two spaced, symmetrical central regions of said body, the symmetrical regions preferably being semi-circular in shape. It is further preferred that the crimped filaments contain a dye that is releasable from the crimped filaments during use to indicate the wear of the brush-head.

In another aspect, the invention features a method of brushing the teeth including contacting the teeth with a plurality of crimped bristles.

In a further aspect, the invention features a crimped bristle for a toothbrush.

In yet another aspect, the invention features a method of making an oral brush. The method includes providing a body dimensioned for insertion into the mouth, providing a filament formed of a material suitable for use in the mouth, imparting a degree of crimp to the filament, forming the filament into bristles, and mounting the bristles on the body.

An "oral brush", as used herein, is any brush that includes a body having a brush portion designed for insertion into the mouth. The brush portion includes a plurality of bristles extending therefrom and being dimensioned to be used to brush tooth surfaces.

According to another aspect of the invention, the oral brush comprises an electric toothbrush. Preferably, the electric toothbrush has a brush head, with a plurality of crimped bristles arranged in a tuft extending from the brush head. In featured embodiments, the brush head has both tufts of crimped bristles and tufts of straight bristles, with at least some of the tufts of straight bristles extending from the brush head beyond the tufts of crimped bristles. Preferably, at least two of the tufts of straight bristles extending beyond the distal ends of the tufts of crimped bristles are separated by a distance of about 10 millimeters.

Suitable electric toothbrushes may include a brush head selected from the group consisting of vibrating, oscillating, and rotating brush heads, or any other conventional brush-head.

In one embodiment, the tufts of crimped bristles are arranged in an inner region of the brush head, surrounded by the tufts of straight bristles arranged in an outer region of the brush head.

Preferably, the tufts of straight bristles each have at least about 8 percent more (and have, in some instances, up to 15 percent or more) bristles than each of the tufts of crimped bristles.

In some embodiments, the tufts of crimped bristles are splayed, at rest, such that they occupy a substantially wider area at their distal ends than at their base ends (i.e., at the body).

In some other embodiments, the oral brush is adapted to rotate the brush head about a rotational axis substantially parallel to the longitudinal axis of the tuft, and to cyclically move the brush head in the direction of the rotational axis.

The term "random" as used herein, does not imply mathematical randomness, but is intended to merely indicate that the condition described is not uniform or regularly repeating, but has some degree of randomness.

The term "stiffness", as used herein, refers to the stiffness of the oral brush when tested in accordance with ISO 8627.

Other features and advantages of the invention will be apparent from the description of the preferred embodiment thereof, and from the claims.

BRIEF DESCRIPTION OF THE DRAWINGS

FIG. 2 is a perspective view of an oral brush according to one embodiment of the invention.

FIGS. 3 and 3A are highly enlarged side views of sinusoidally crimped bristles that are arranged in-phase and out-of-phase, respectively.

DESCRIPTION OF PREFERRED EMBODIMENTS

Referring to FIG. 2, a toothbrush 10 includes a plastic body having a handle 12 and a head 14 attached to a bristle portion 16.

The body of the toothbrush is formed by conventional methods well-known in the art. The handle is shaped to be grasped by a hand, but alternatively can be shaped to fit into an electric toothbrush. The configuration of the head can vary and may be rectangular, oval, diamond-shaped, or any other shape, with bristles which are trimmed flat, V-shaped, serrated, convex curved, or any other desired topography. The shape and size of handle 12 and head 14 can vary and the axes of the handle and head may be on the same or a different plane. The bristle portion is formed of one or more tufts of individual bristles attached to the head in manners known to the art, e.g., stapling or hot-tufting.

Bristle portion 16 includes a number of crimped bristles. Any material suitable for use in oral brush bristles may be used to form the crimped bristles, provided that a degree of crimp can be imparted to the material. Suitable materials include, but are not limited to, Nylon 612, PBT, PVDF, acetyl resins, polyesters, fluoropolymers, polyacrylates, polysulfones, and mixtures thereof. Preferred materials are capable of retaining the crimp imparted during normal use of the oral brush, and, when crimped, have the stiffness characteristics desired for a particular application. The bristles may contain PTFE, kaolin, or other fillers or additives. The bristles may each comprise a blend of polymers, or bristles comprising different polymers may be mounted on the same oral brush. If the bristles comprise a blend of polymers, the individual polymers may either be blended to form a single phase, or maintained in separate phases and coextruded together in any desired configuration, e.g., with one polymer forming a sheath surrounding another polymer (sheath/core) or side-by-side.

The bristles preferably have substantially uniform cross-sectional dimensions between about 0.004 inch to about 0.015 inch. Preferably the crimped bristles have a stiffness grade (ISO 8627) of from about 2 to 7 $cN/mm^2$.

Figure 1A:
FIG. 1A is a highly enlarged optical micrograph of a straight bristle according to the prior art.
Figure 1B:
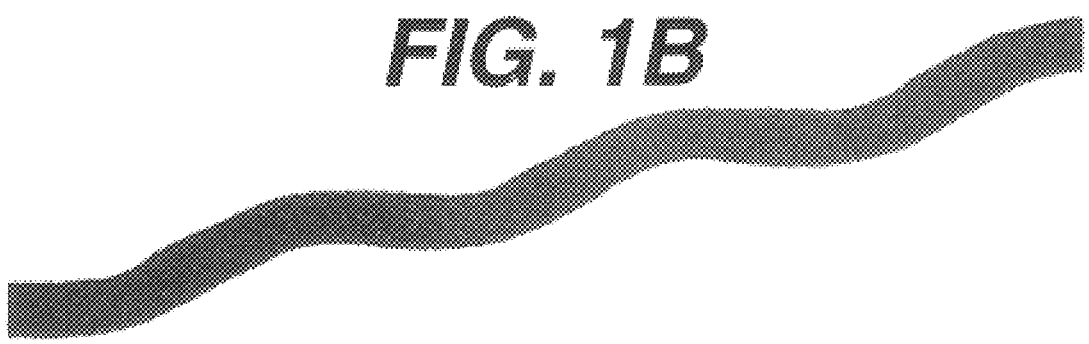
FIG. 1B is a highly enlarged optical micrograph side view of a structurally crimped bristle.

As shown in FIGS. 3 and 3a, in preferred embodiments the crimp is substantially sinusoidal. The sinusoidal crimp preferably has an amplitude of from 0.01 to 1.0 mm and a frequency of 0.5 to 50 crimps/cm. When the crimp is structural, as shown in FIG. 1B, the crimp width is equal to the reciprocal of the frequency. Neighboring bristles may be aligned, so that the sine waves are in-phase (FIG. 3), or offset so that the sine waves are out-of-phase (FIG. 3A), or any desired combination of these configurations.

Figure 1C:
FIGS. 1C and 1D are, respectively, highly enlarged top and side views of a surface crimped bristle.
Figure 1D:
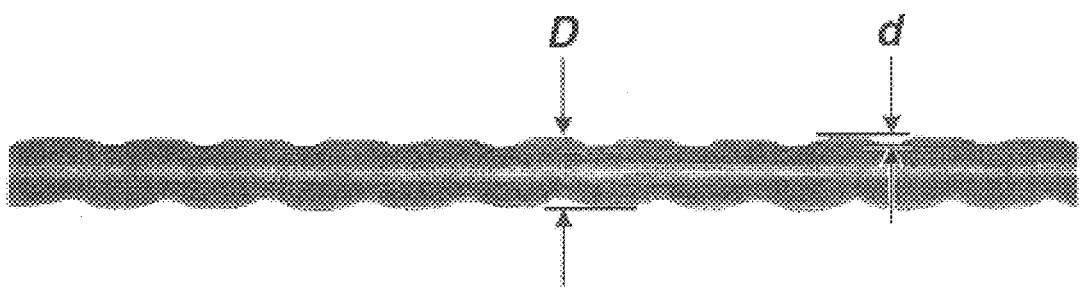
Figure 1E:
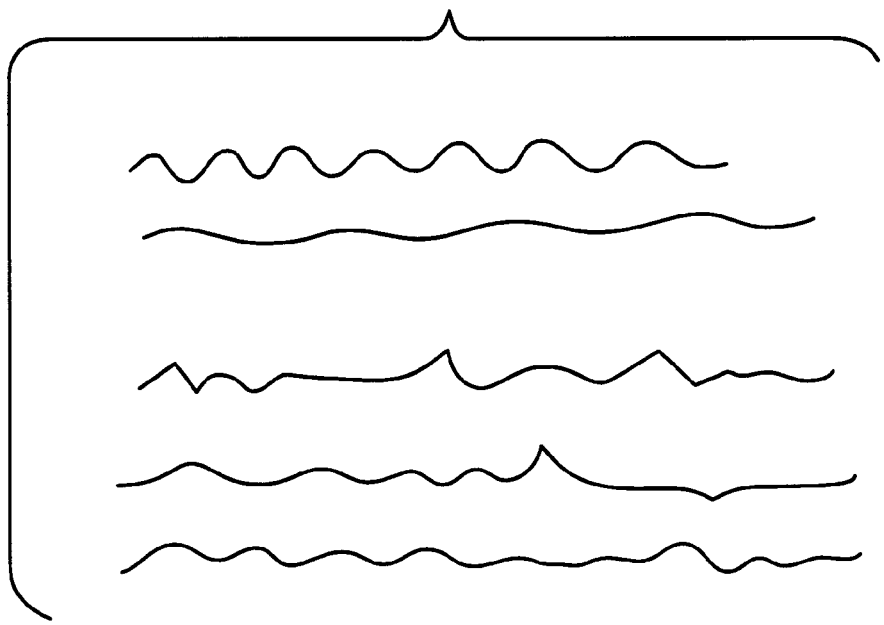
FIG. 1E is a highly enlarged schematic side view of bristles having different crimp configurations.

Alternatively, the crimp may be surface crimp, as shown in FIGS. 1C and 1D. In this case, the frequency is preferably from 1 to 50 crimps/cm, the width is preferably from 0.05 to 2.0 mm, and the ratio of the depth of the crimp (d) to the diameter of the bristle (D) is from about 0.01 to 0.2. The deformations may be substantially rectangular in cross-section, as shown, or may be hemi-spherical or any other desired type of deformation.

Figure 1F:
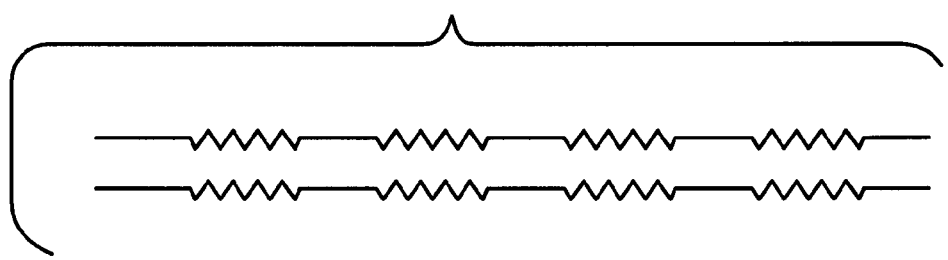
FIG. 1F is a highly enlarged schematic side view of a bristle having intermittent structural crimp.

As shown in FIG. 1F, the crimp can be intermittent, i.e., the bristle may include portions that are crimped and portions that are not crimped, at regular intervals or arranged in any desired manner. Having straight portions may facilitate insertion of the bristles into bristle holes in the toothbrush head without excessive fanning out of the bristles due to the crimp. Preferably, the intermittently crimped filament would be cut into bristles at approximately the midpoints of the crimped portions, and each bristle folded in half so that the straight portion could be inserted into the tuft holes in the head.

Suitable methods of imparting crimp include mechanical, thermal and chemical methods. Crimping techniques are well known in the general filament forming art and include: false twisting the filaments, heating them and then untwisting them; gear crimping; neck drawing; passing the filaments through a stuffer box; and asymmetric quenching of the filaments.

Figure 4:
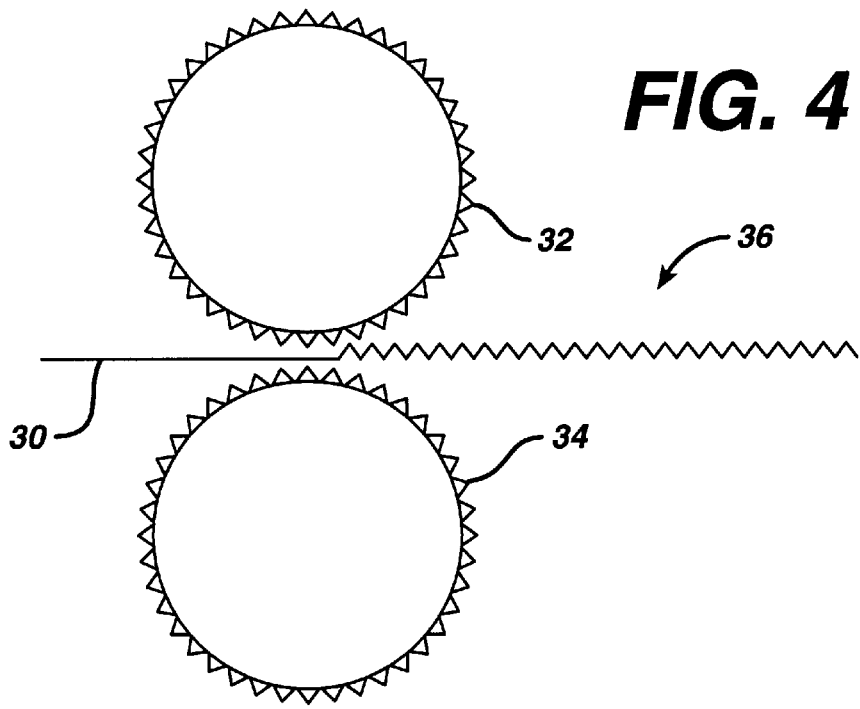
FIG. 4 is a diagrammatic view of a method of imparting crimp to a filament according to one embodiment of the invention.

One method of imparting crimp to filaments by gear crimping is shown in FIG. 4. According to this embodiment of the invention, a filament 30 is passed through a pair of opposed gears 32,34 which impart a crimp 36 to the filament as is well known in the textile industry. The spacing between the gears can be adjusted to adjust the level of crimping obtained. The teeth of the gears can be regular or irregular, depending upon the regularity of crimp desired. One gear can have no teeth, or differently spaced teeth, if desired.

Figure 5:
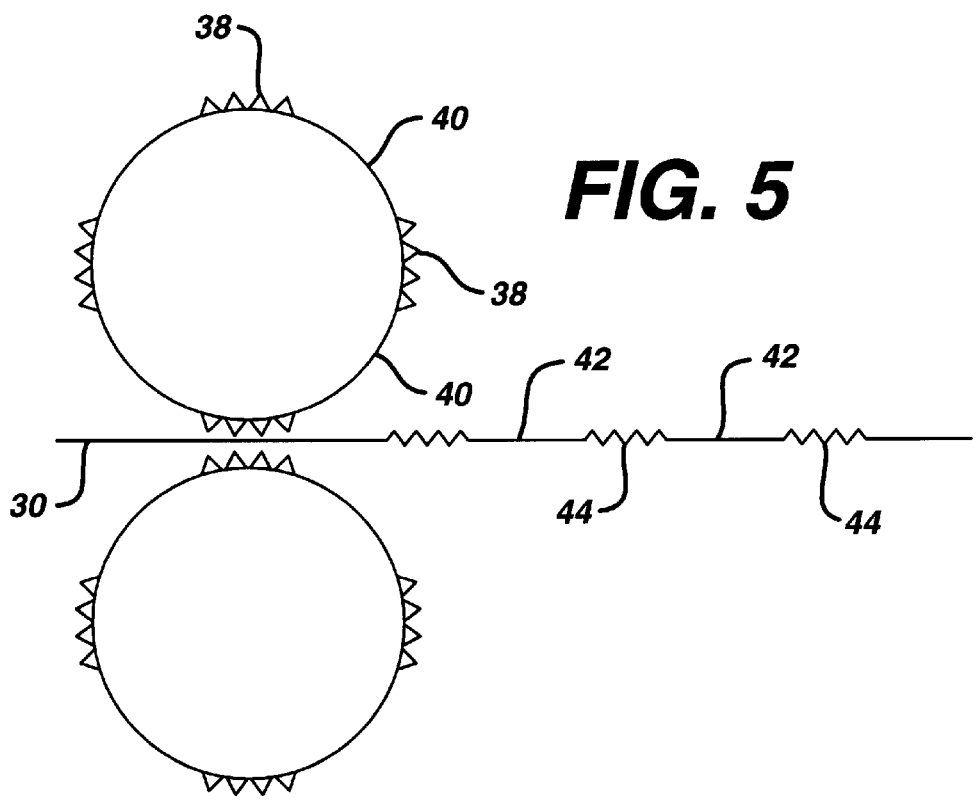
FIG. 5 is a diagrammatic view of a method of imparting intermittent crimp to a filament.

A method of imparting intermittent crimp is shown in FIG. 5. This method is similar to that shown in FIG. 4, but the teeth of the gears are intermittent rather than continuous, i.e., the teeth are arranged in sets 38, having gaps 40 therebetween. As a result, the filament exiting the gears includes straight portions 42 (corresponding to the gaps 40) and crimped portions 44 (corresponding to the teeth 38).

The following examples are intended to be illustrative and are not intended to limit the scope of the invention.

EXAMPLE 1

A brush was made of 0.007 inch diameter nylon 612 filaments having a mean frequency of 5.6 crimps/centimeter and a mean amplitude of 0.15 millimeter (see Table 1 for measurements of individual filaments, on which these means were based).

TABLE 1

Measurements of Selected Crimped Bristles

| Bristle | Frequency (crimps/cm) | Amplitude (mm) |
| --- | --- | --- |
| 1 | 5.6 | 0.153 |
| 2 | 5.7 | 0.164 |
| 3 | 5.5 | 0.161 |
| 4 | 5.6 | 0.151 |
| 5 | 5.5 | 0.131 |
| Mean | 5.6 | 0.152 |

The stiffness grade (tested according to ISO 8627) of this brush was about 20% less than a comparable brush made with straight 0.007 inch thick nylon 612 filaments, and about 40% less than a comparable brush made with straight 0.008 inch thick nylon 612 filaments (see Table 2).

TABLE 2

Stiffness Grade of Oral-B P-35 Brushes With Different Bristles

| Diameter (mil) | Stiffness Grade[1] (cN/mm$^2$) Straight | Crimped |
| --- | --- | --- |
| 6 | 3.8$^c$, 3.5$^d$ | 2.8$^b$, 2.5$^c$ |
| 7 | 4.6*$^c$, 4.6*$^d$ | 3.5$^a$, 3.8$^b$, 3.7$^c$ |
| 8 | 5.4$^c$, 5.75$^d$ 5.8$^a$, 5.9$^b$ | 5.0$^b$, 4.6$^c$ |

[1]ISO 8627 (dry conditions only)
$^{a-d}$Values from sets of brushes run at different times
*Interpolated values from indicated brush sets
$^a$Brush set from clinical trial in Example 2

EXAMPLE 2

A brush with crimped 0.007 inch diameter nylon 612 filaments and a brush with straight 0.008 inch diameter nylon 612 filaments, as described in Example 1 above, were tested in a clinical trial with 30 panelists. The trial was a crossover study in which panelists were randomly assigned a brush and asked to follow their normal oral hygiene routine for six days. After the six days had elapsed, the panelists refrained from normal oral hygiene for 24 hours and then visited the dental clinic. At the clinic, plaque was scored using the Turesky modification of the Quigley-Hein plaque index (see Turesky, S., Gilmore N. D., Glickman I., "Reduced Plaque Formation by the Chloromethyl Analogue of Vitamin C," *J. Periodontal*. 41:41–43 (1970)) before and after brushing for one minute with the assigned brush. The mean results for overall plaque are shown in Table 3. The results for overall plaque removal (delta P) showed a 5.3% improvement for the brush with crimped bristles, even though the stiffness was 40% less (see Example 1).

TABLE 3

Clinical Results for Overall Plaque Using Brushes with Crimped and Straight Filaments

| Brush | $P_B^1$ (SD) | $P_A^2$ (SD) | $\Delta P^3$ (SD)[4] |
| --- | --- | --- | --- |
| Straight | 1.76 (0.40) | 0.42 (0.28) | 1.33 (0.41) |
| Crimped | 1.94 (0.36) | 0.54 (0.48) | 1.40 (0.37) |

$^1P_B$ = mean plaque score before brushing
$^2P_A$ = mean plaque score after brushing
$^3\Delta P = P_B - P_A$
$^4$SD - standard deviation The toothbrush may include other types of non-crimped bristles in combination with the crimped bristles, e.g., gum-massaging bristles or conventional straight bristles. The crimped bristles can be located in some or all of the perimeter tufts to provide softness against the gums, or can be located in some or all of the inner tufts to provide fullness. Moreover, although sinusoidal crimp has been illustrated above, the bristles may have other types of crimp, e.g., the crimp may have a different non-random shape, e.g., square waves, or may be random. Although generally, for ease of manufacture, all of the bristles of the brush will have the same crimp geometry, bristles having different crimp geometries may be combined if desired.

Figure 6:
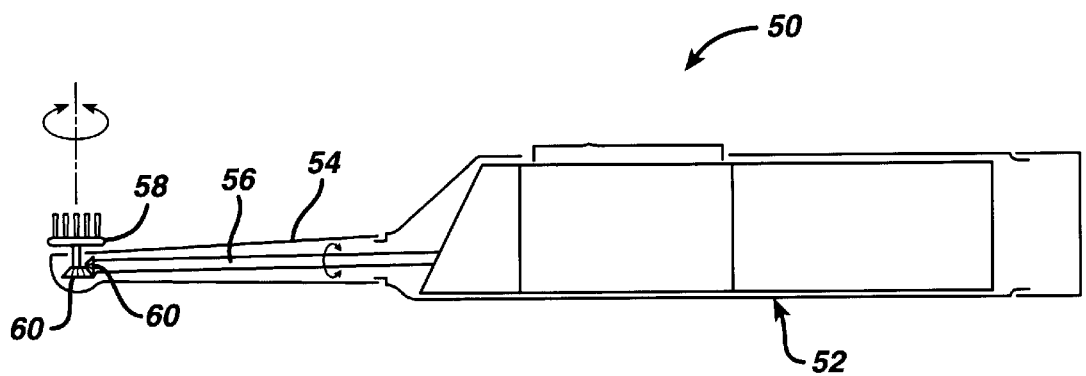
FIG. 6 is a schematic side view of an electric toothbrush according to one embodiment of the invention.

The oral brush need not be a manual toothbrush having a conventional shape, as shown in FIG. 1, but may be any type of brush designed for brushing teeth that includes a body with bristles extending therefrom. For example, the toothbrush may be any type of electric toothbrush, e.g., a toothbrush 50 having a body 52, a neck 54, a drive shaft 56, and a head 58 operably connected to the drive shaft 56 by a pinion gear 60, as shown in FIG. 6. Head 58 includes a plurality of crimped bristles, and may also, optionally, include a plurality of non-crimped bristles.

Figure 6A:
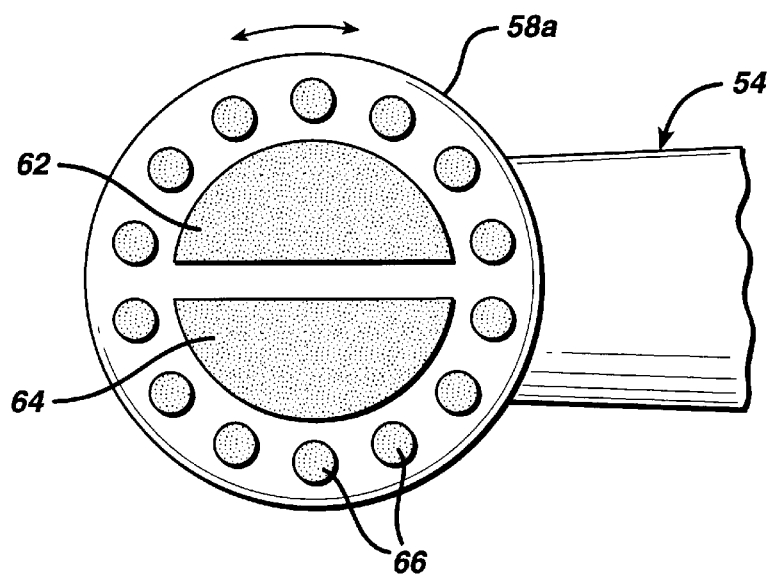
FIG. 6A is an enlarged top view of a first embodiment of the brush head of the toothbrush of FIG. 6.
Figure 6B:
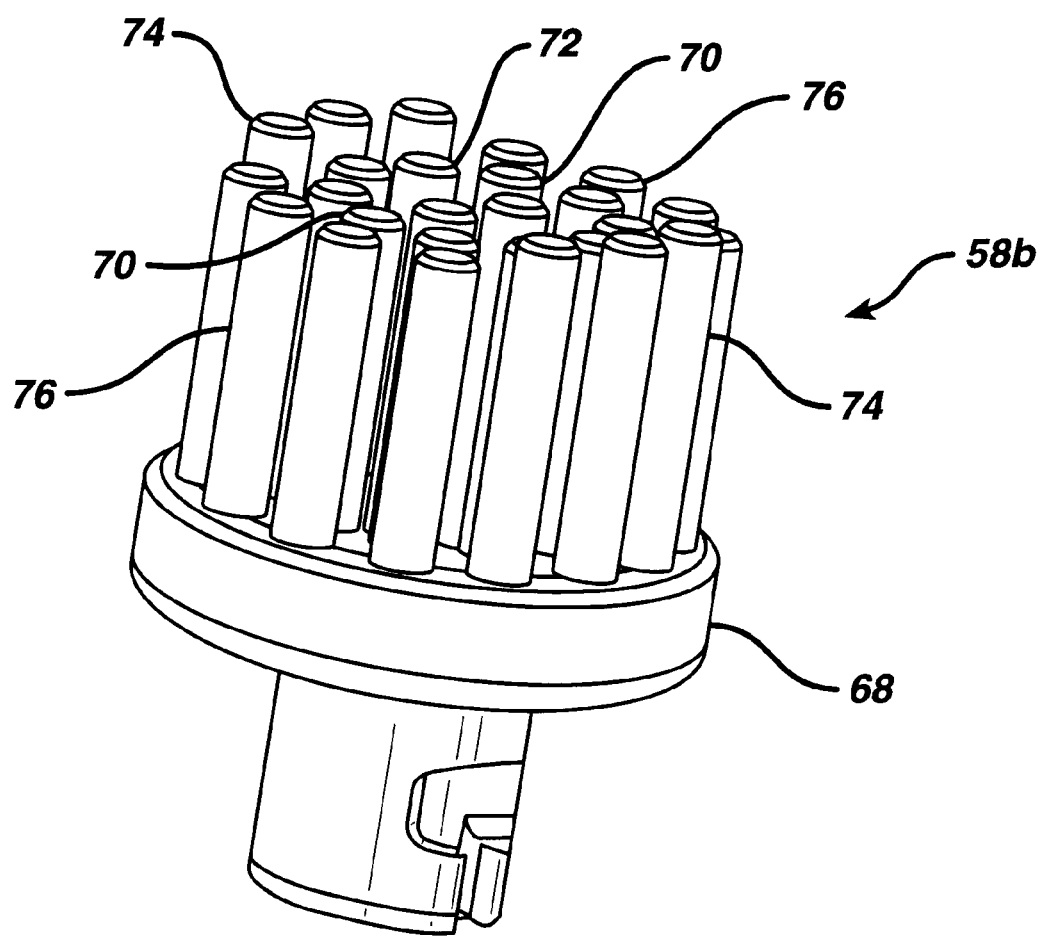
FIG. 6B is an enlarged perspective view of a second embodiment of the brush head of the toothbrush of FIG. 6.

Examples of preferred electric toothbrush heads 58a and 58b are shown in FIGS. 6A and 6B. Head 58a (FIG. 6A) includes a plurality of tufts of crimped bristles defining a pair of substantially semi-circular brush portions 62 and 64, and further includes a plurality of tufts 66 of non-crimped bristles disposed about the periphery of the head.

Figure 7:
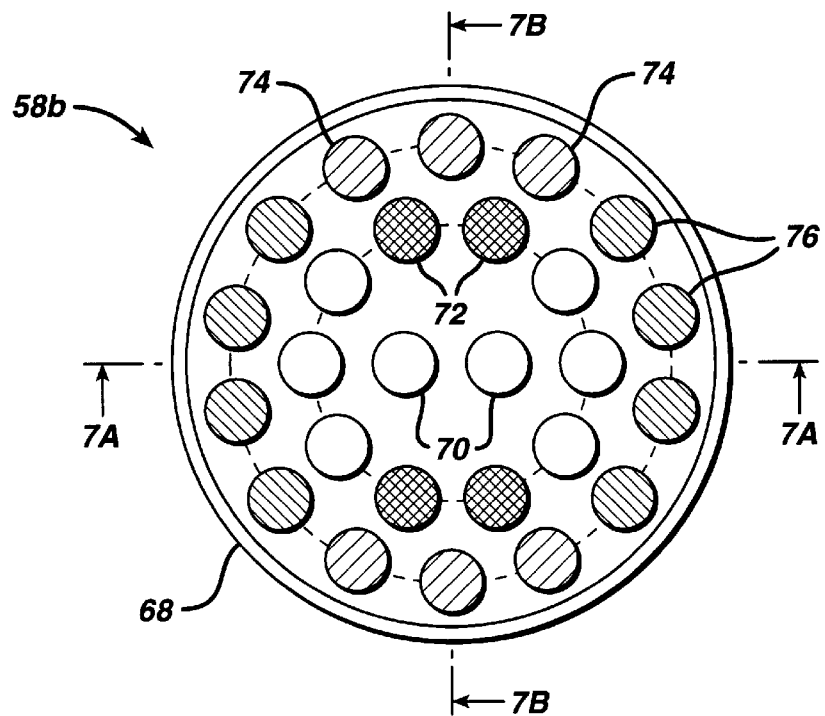
FIG. 7 is a top view of the brush head of FIG. 6B.
Figure 7A:
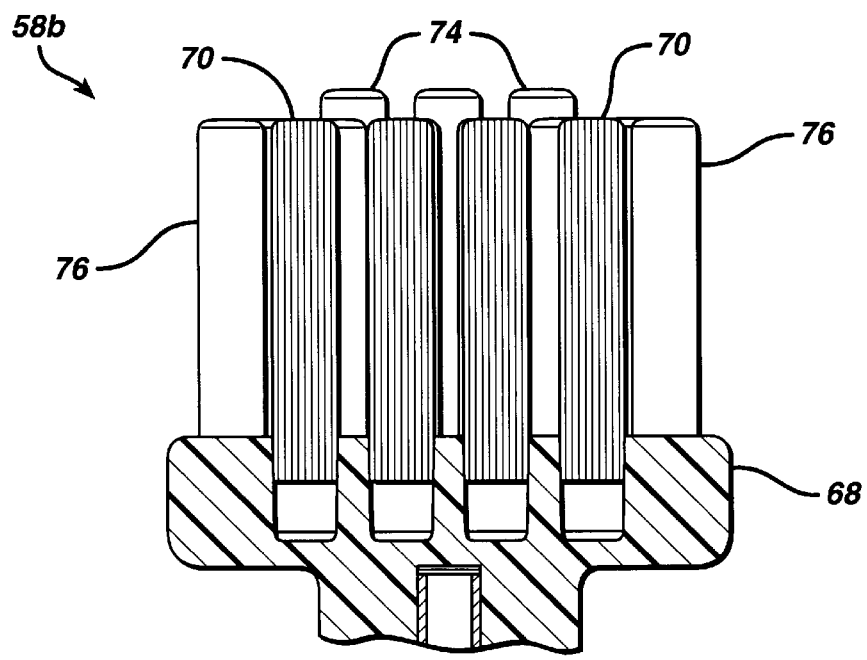
FIGS. 7A and 7B are cross-sectional views, taken along lines 7A–7A and 7B–7B, respectively, of FIG. 7.
Figure 7B:
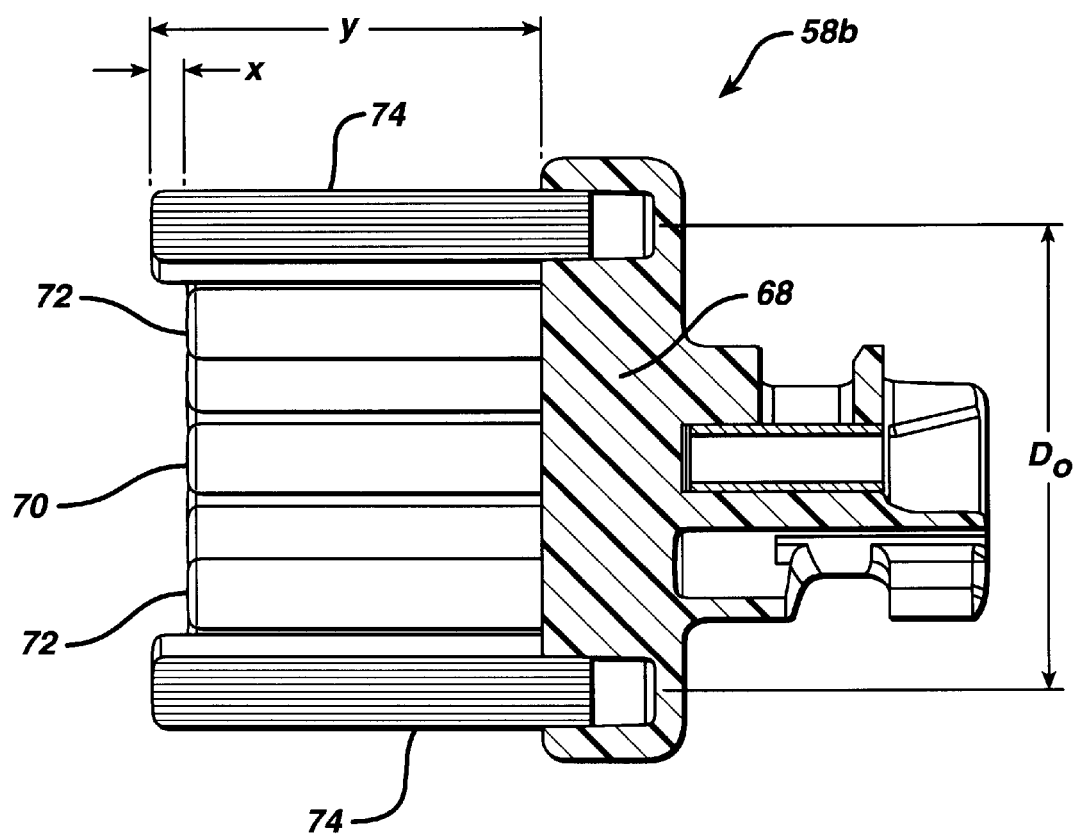

As shown in greater detail in FIGS. 7, 7A and 7B, head 58b has an array of tufts 70 of crimped bristles extending from a body 68 and arranged with tufts 72 and 74 of straight bristles dyed with a wear indicator, and tufts 76 of undyed straight bristles. (The different types of tufts are shown with different cross-hatching for illustration in FIG. 7.) Crimped tufts 70 and straight dyed tufts 72 make up the inner field of tufts, while straight dyed tufts 74 and straight undyed tufts 76 make up the outer row of tufts. As seen in FIGS. 7A and 7B, outer, straight dyed tufts 74 are longer by a distance, x, of about 0.7 millimeters, than the other tufts of the head, and have an overall exposed length, y, of about 8.2 millimeters. The diameter $D_0$ of the outer ring of tufts is preferably about 10.2 millimeters to correspond to a typical width of a tooth. In this configuration, the individual crimped bristles of tufts 70 have about 18 crimps per inch (7 crimps/centimeter), with a crimp amplitude of about 0.0035 inch (0.09 millimeter). Preferably, tufts 70 each have about 46 bristles, tufts 72 and 74 each have about 52 bristles, and tufts 76 each have about 54 bristles. Many other arrangements of crimped and non-crimped bristles can also be used, as would be understood by a person skilled in the art.

Figure 8:
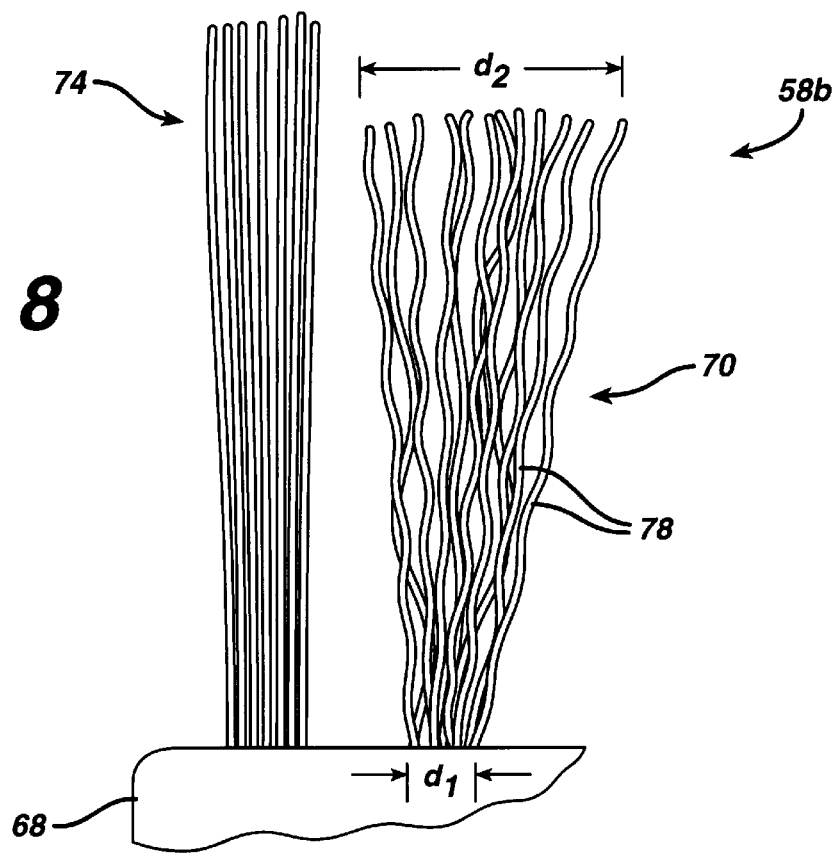
FIG. 8 shows a tuft of crimped bristles adjacent a tuft of straight bristles.

Although the tufts of bristles in the above figures are illustrated as having a generally cylindrical shape, tufts of structurally crimped bristles tend to have more of a conical shape, illustrated in FIG. 8. Due to the deformations of the structurally crimped bristles, especially those near head body 68, individual crimped bristles 78 of the tuft tend to be splayed away from each other, such that the tuft assumes an overall conical form, enlarging from a diameter $d_1$ at the base of the tuft to a diameter $d_2$ at the top of the tuft, with the axes of the individual crimped bristles being less parallel than in tufts of straight bristles. One advantage of this effect is that the crimped tuft occupies more space, as viewed from its distal end, giving the brush a fuller, more dense appearance. Additionally, because of the splaying of the bristles and the axial undulations of the individual, structurally crimped bristles, the bristles are each directed, at their very distal tips, in different directions. The benefit of this multi-directional tip orientation is explained below.

Figure 9A:
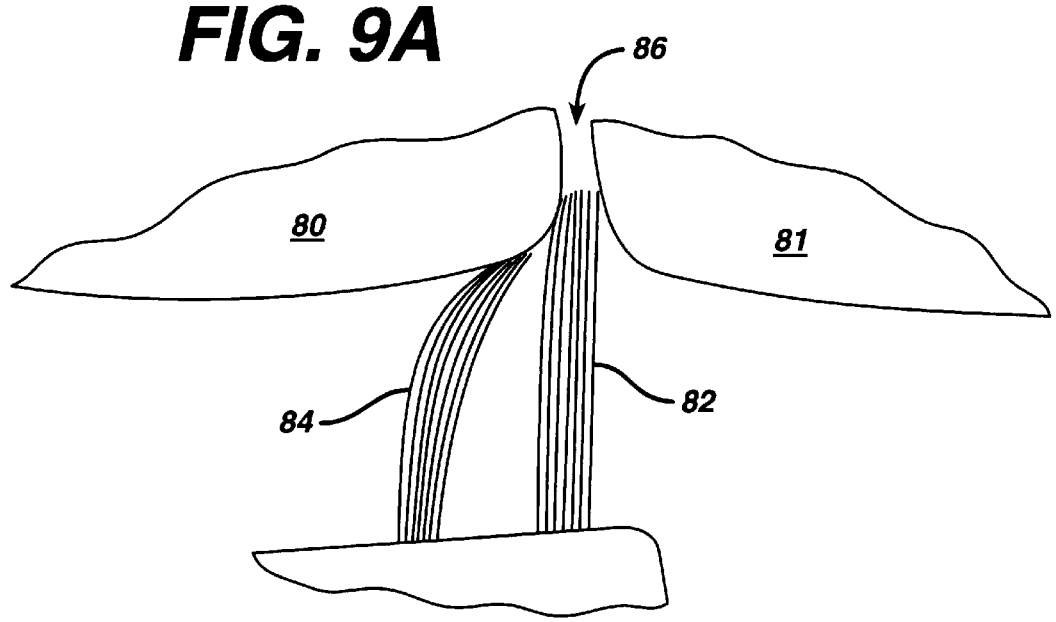
FIGS. 9A and 9B illustrate the flexing of a tuft of straight bristles and a tuft of crimped bristles, respectively, when loaded against a tooth surface.
Figure 9B:
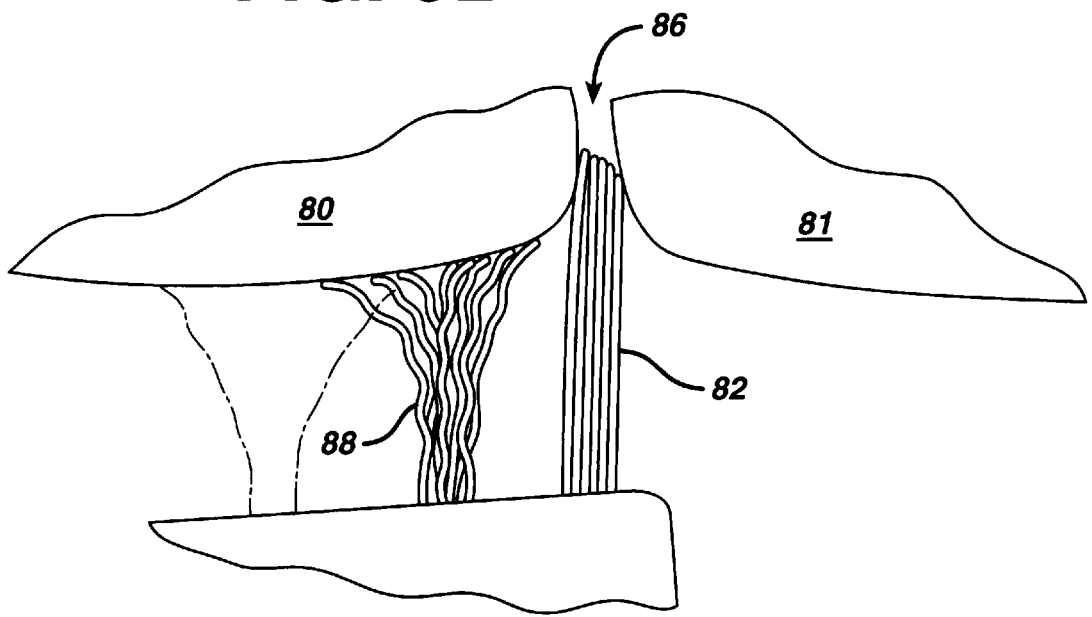

Another benefit of combining crimped tufts and straight tufts is illustrated by comparing FIGS. 9A and 9B. In each of these figures, two adjacent tufts of bristles are shown, loaded against the surface of a tooth 80 with a force applied generally in the direction of the bristles (i.e., a normal load). In FIG. 9A, both tufts 82 and 84 have straight bristles. In the loaded position, tuft 82 is shown extending into the gap 86 between tooth 80 and an adjacent tooth 81. The distal ends of tuft 84, however, are loaded directly against the surface of tooth 80, causing tuft 84 to be bowed toward tuft 82. Because of the close spacing and identical structure of all of the bristles in tuft 84, and because their distal ends tend to contact tooth 80 in the same general area, the bristles tend to be bowed in the same direction, with outer portions of some bristles laying along the surface of the tooth, being pressed against, in turn by outer portions of other bristles. The net effect is that the distal ends of some of the bristles in tuft 84 are loaded more than others, increasing their tendency to wear.

In FIG. 9B, tuft 84 of FIG. 9A has been replaced by a tuft 88 of structurally crimped bristles. Because the axes of the crimped bristles of tuft 88 are much less parallel than the axes of straight bristles in a tuft, and because of the multi-directional orientation of the distal tips of the bristles, as described above, the crimped bristles of tuft 88 tend to be splayed in different directions when loaded directly against the tooth surface. The end portions of the bristles of tuft 88 therefore tend to extend to cover a larger surface area of the tooth, overlapping to some extent another tuft of crimped bristles, shown in dashed lines. There is also less of a tendency for the splayed, crimped tuft 88 to press against and deflect outer tuft 82 than the bowed, straight tuft 84 of FIG. 9A. Furthermore, because of the above-described structure of tuft 88, its resistance to displacement when loaded directly against a tooth surface tends to be lower than with typical tufts of straight bristles, which may result in, for the same applied load, greater deflection and therefore higher penetration of adjacent straight tuft 82 into gap 86.

Simulated wear tests were conducted, using brush head 58b of FIG. 6B with a commercial electric toothbrush. After an equivalent of 20 weeks of normal brushing, the brush head with crimped tufts 70 showed lower wear than an identical head with standard straight tufts in place of tufts 70. The wear index (a parameter used to quantify such wear tests) was reduced from 32 percent (with all straight bristles) to 25 percent (with the configuration shown in FIG. 6B).

In this manner, effectively softer tufts of bristles can be combined with effectively stiffer tufts, with bristles of all tufts being of about the same diameter of, for instance, 0.00625 inch (0.16 millimeter). Keeping all bristles of about the same diameter aids in the end-rounding process, in which the distal ends of all bristles are rounded after assembly for improved feel.

In vitro plaque removal tests were conducted to compare the plaque-removing abilities of electric toothbrushes having brush heads with and without tufts of crimped bristles. Brushes with inner fields having crimped bristles demonstrated significantly better plaque-removing capabilities. Advantages of crimped bristles appeared, for instance, in the tests relating to the occlusal (i.e., biting) surfaces of the molars and premolars, in which there was notably better penetration of the occlusal fissures. On the buccal and lingual sides of the teeth, the brush heads with crimped bristles showed increased brushing action in the interdental areas, apparently due to the improved penetration of the outer, longer tufts of bristles as illustrated in FIG. 9B.

Figure 10:
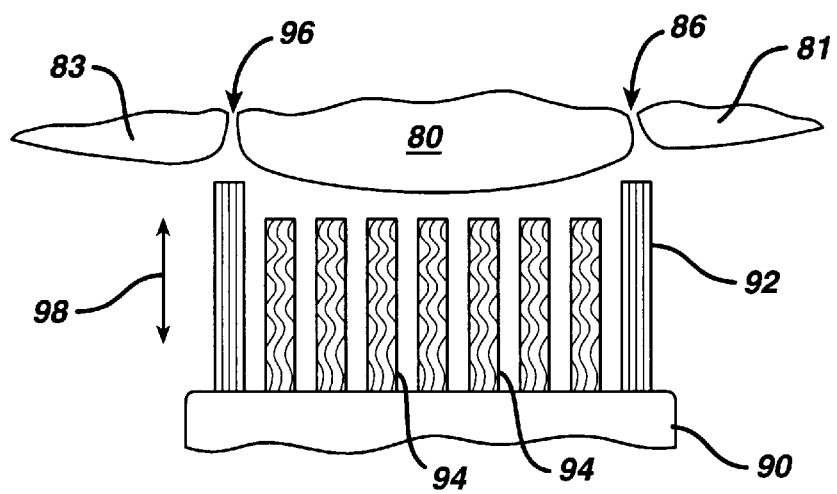
FIG. 10 shows an array of tufts of straight and crimped bristles being cyclically loaded against a tooth surface.

The above configuration of bristle tufts has particular advantages in a bristle head (e.g., head 58b of FIG. 6B) that is moved against the tooth surface in a cyclic motion toward and away from the surface of the tooth (i.e., in the direction of the bristles), as well as in a rotary motion. Referring to FIG. 10, a brush head 90 has outer tufts 92 of straight bristles and inner tufts 94 of crimped bristles. (For purposes of illustration, all of the tufts are shown schematically). Because of the spacing between opposing outer tufts 92, the outer tufts are shown to roughly line up with neighboring gaps 86 and 96 between adjacent teeth 80 and 81, and 80 and 83, respectively. As brush head 90 is cycled toward and away from tooth 80 (as suggested by arrow 98), crimped tufts 94 are loaded substantially directly against the surface of tooth 80, and straight tufts 94 extend into gaps 86 and 96.

As explained above with respect to FIG. 9B, this loading causes crimped tufts 94 to be splayed outward. So cyclically splayed, the distal ends of the bristles of tufts 94 extend and retreat along the surface of tooth 80 and between tooth 80 and adjacent gum tissue, helping to loosen and remove debris.

When such a brushing motion is provided by an electric toothbrush, the low effective stiffness of the crimped, inner tufts helps to absorb the cyclic load between the tooth surface and the handle of the toothbrush, such that there tends to be less discomforting vibration imparted to the hand of the user. An example of such an electric toothbrush applicable to the invention is shown in FIGS. 11 through 15 and described below.

Figure 11:
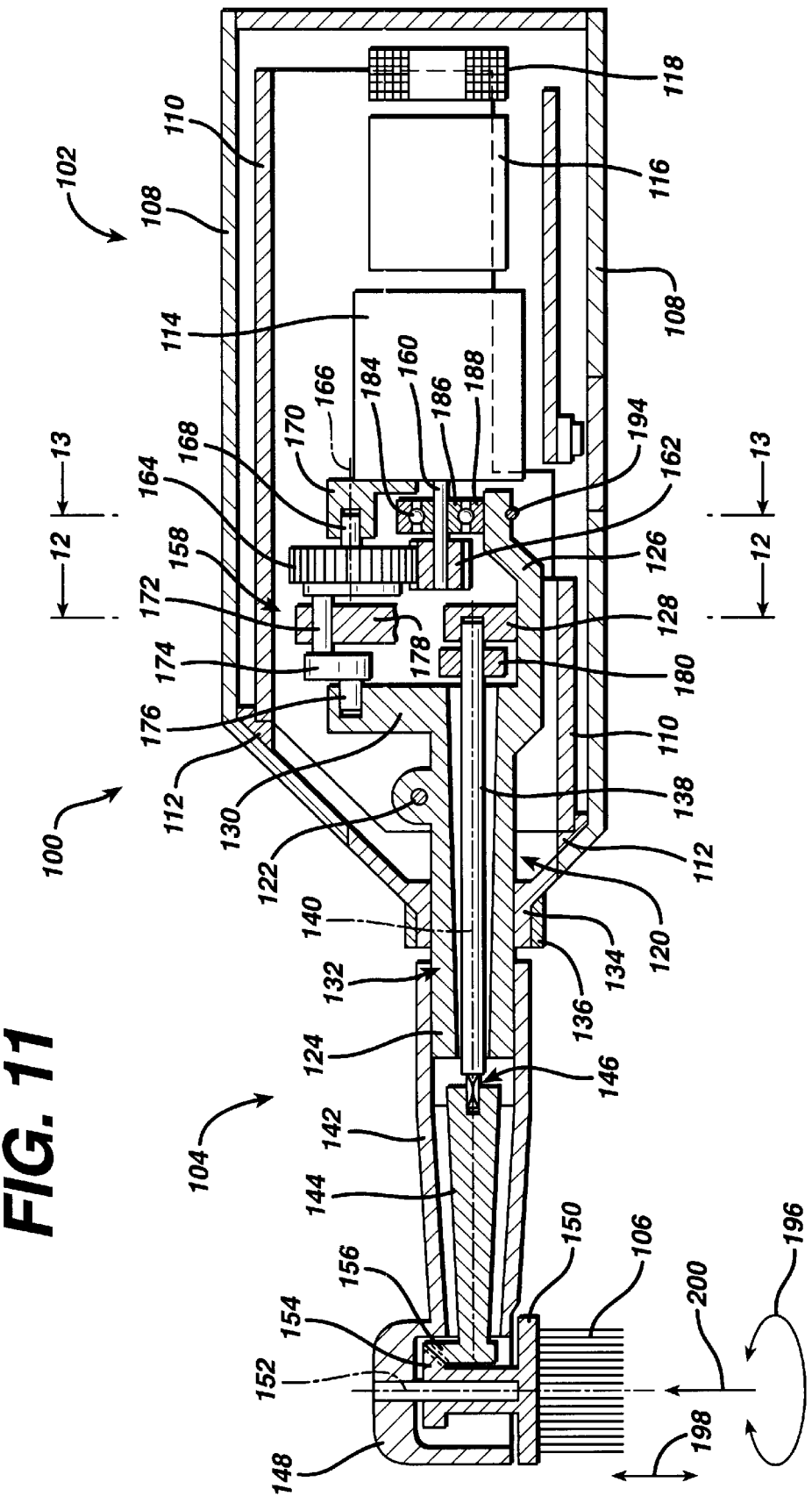
FIG. 11 is a schematic illustration, along a longitudinal section, of a first design example of an electric toothbrush.
Figure 12:
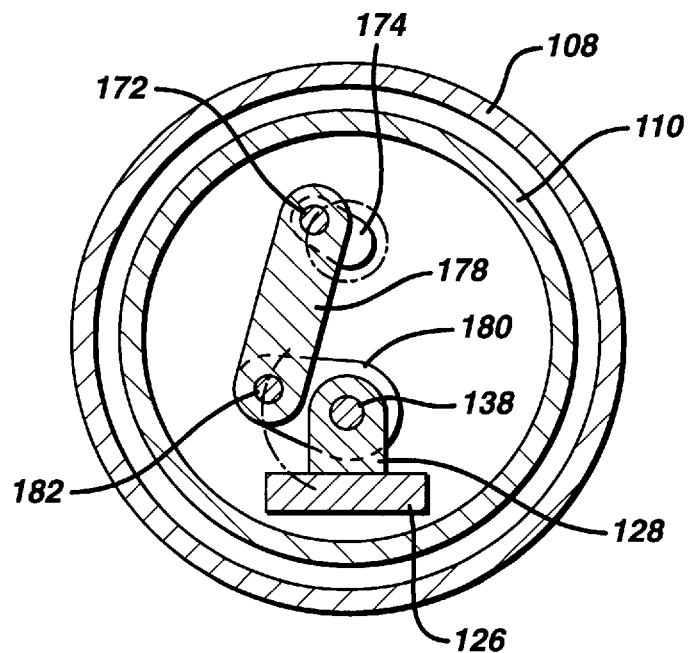
FIGS. 12 and 13 are cross-sectional views, taken along planes 12—12 and 13—13, respectively, in FIG. 11.
Figure 13:
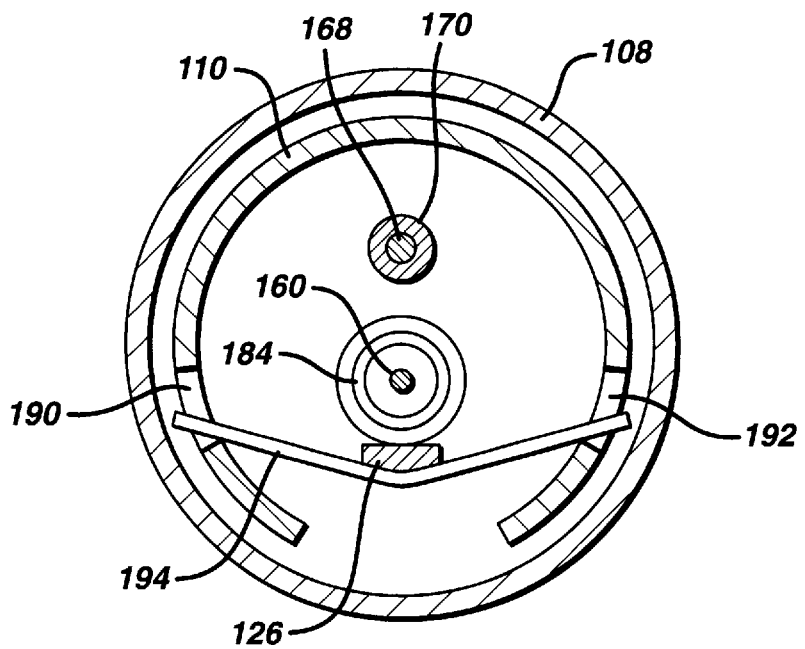

FIGS. 11 through 13 show a first design example of an electric toothbrush 100, serving to clean a user's teeth, and to remove plaque from dental surfaces.

The electric toothbrush includes a roughly cylindrical, elongated handle 102. A brush attachment 104, itself in roughly cylindrical, elongated form, can be mounted on handle 102. The diameter of the handle is so chosen that a user can hold the electric toothbrush by the handle securely in his or her hand. The diameter of the brush attachment 104 is smaller than the diameter of the handle to permit easy insertion of the brush attachment into the user's mouth.

At the free end of the brush attachment 104, a multiplicity of bristles 106 protrude from the bristle head, serving to clean the user's teeth.

The handle 102 incorporates a housing 108, which accommodates a frame 110. The frame is elongated and partly cylindrical, and extends over almost the entire length of the housing, and thus of the handle. At its end facing brush attachment 104, frame 110 is elastically held in place in housing 108 by cushions 112, of plastic or rubber or a similar material.

Attached to frame 110 are an electric motor 114, a battery 116 and additional electronic components such as a charging coil 118 and the like. These components are arranged one behind the other in the longitudinal direction of handle 102. Also attached to the frame is a rocker arm 120, which can swivel around a spindle 122. The rocker arm and spindle are located in the section of handle 102 that faces brush attachment 104. Part of rocker arm 120 protrudes from handle 102.

Rocker arm 120 incorporates a tube 124, a cantilever 126, and two support stems 128 and 130. Tube 124 of rocker arm 120 extends through an opening 132 in the end of handle 102, facing brush attachment 104, and protrudes from the handle. Located between tube 124 and housing 108 of the handle is an annular diaphragm 134, made of plastic, rubber or a similar material, by way of which tube 124 extends elastically from the handle. Holding and retaining the tube in the housing is a clamp 136, which surrounds the diaphragm in ring-shaped fashion.

At least that part of tube 124 that extends from handle 102 has a cross section that is contoured on the outside. It is on this protruding part of the tube that brush attachment 104 can be mounted. At its end that faces the handle, the brush attachment has a cross section that is contoured on the inside in such a way as to match the outer contour of tube 124. The matching contours are formed in such a way that the brush attachment can be mounted on the handle in only one particular angular position. For example, the contour may have a star-shaped, or triangular, or similar configuration.

When mounted on tube 124 of rocker arm 120, brush attachment 104 becomes an integral part of the rocker arm. Located in tube 124 is a shaft 138, which is pivot-mounted at one end, on the free end of the tube, protruding from handle 102 and, at the other end, on support stem 128. Shaft 138 extends roughly in the longitudinal direction of the handle and brush attachment 104, and defines an axis 140. The shaft constitutes another component of rocker arm assembly 120. This shaft protrudes from tube 124 where, at its free end, it is contoured on the outside.

The axis of spindle 122 of rocker arm 120, and axis 140 of shaft 138 extend roughly perpendicular to each other.

Tube 124 of rocker arm 120 accepts brush attachment 104. The brush attachment is provided with a support tube 142, in which a brush shaft 144 is pivot-mounted. When the brush attachment is mounted, brush shaft 144 is concentric with axis 140. At its end facing handle 102, the brush shaft has a recess 146. This recess has a cross section with an inside contour which corresponds to the outer contour of shaft 138 that protrudes from tube 124. The matching contours are configured in a way that shaft 138 can be inserted in recess 146 in several angular positions. For example, the contour may be square.

The free end of support tube 142, and thus the free end of brush attachment 104, holds a receptacle 148 which houses a bristle head 150 with bristles 106. Bristle head 150 is disk-shaped, and can swivel about a pin 152. Pin 152 extends through the center of the disk of the bristle head. Bristles 106 extend away from the bristle head, approximately parallel with pin 152.

Pin 152 of bristle head 150 extends roughly perpendicular to axis 140 of shaft 138, and also approximately perpendicular to spindle 122 of rocker arm 120.

By way of two bevel gear segments 154 and 156, an alternating rotary movement of brush shaft 144 about axis 140 can be translated into an alternating rotary movement of bristle head 150 about pin 152.

It should be noted that such translation of the alternating rotary movement from brush shaft 144 to bristle head 150 can be accomplished in other ways as well. It is possible, for example, to perform this translation in accordance with the aforementioned prior art described in the international patent application WO 94/12121 A1, particularly as shown in FIGS. 1 and 7 of that document. To that extent, patent application WO 94/12121 A1 is incorporated herein by reference.

Between rocker arm 120 and electric motor 114, the handle houses a quadrilateral link 158. In adaptation thereto, electric motor 114 has a motor shaft 160 which extends approximately parallel with axis 140 of shaft 138, and protrudes from the electric motor in the direction of rocker arm 120. Rotationally fixed on the motor shaft is a pinion 162, which meshes with a spur gear 164. Spur gear 164 is pivot-mounted on a shaft 166 which extends approximately parallel with motor shaft 160. A lug 168, positioned in a support stem 170 that is held by the electric motor, extends from spur gear 164 concentric with shaft 166.

On the side of spur gear 164 opposite lug 168, a drive crank 172 is attached to the spur gear, extending essentially parallel with, but at a distance from shaft 166. This crank is also pivot-mounted in the support stem 130 of rocker arm 120, by way of a connector 174 and a tenon 176. Tenon 176 is concentric with shaft 166.

A connecting rod 178 is attached in a rotating form to crank 172. As can be seen especially in FIG. 12, connecting rod 178 is swivel-connected to a crank 180 by means of a pin 182. Between tube 124 and support stem 128, crank 180 is fixed to shaft 138 of the rocker arm.

A ball bearing 184 is mounted on motor shaft 160 of the electric motor. The ball bearing has an eccentric inner race 186 and a concentric outer race 188. It is with eccentric inner race 186 that ball bearing 184 is seated on the motor shaft. The eccentric inner race thus acts as the imbalance. Concentric outer race 188 is in contact with the free end of cantilever 126 of rocker arm 120.

As can be seen especially in FIG. 13, frame 110 is provided with openings 190 and 192, which hold a leaf spring 194 in place by its free ends. Leaf spring 194 is positioned in a way that it bears on cantilever 126 of rocker arm 120, pressing it against outer race 188 of ball bearing 184. The pressure with which the leaf spring pushes the cantilever against the ball bearing is a function of the elasticity constant of leaf spring 194.

When the electric toothbrush 100 per FIGS. 11 through 13 is switched on, motor shaft 160 of electric motor 114 is set in rotating motion. By means of quadrilateral link 158, this continuous rotation is translated into an alternating rotary movement of shaft 138 about axis 140. When brush attachment 104 is mounted, this alternating rotary movement is transferred, by way of bevel gear segments 154 and 156, to bristle head 150, which thus turns in an alternating rotary movement 196 about pin 152. The bristle head turns in an alternating rotary movement within an angle of rotation the range of which may be between about ±15° and about ±40°. The overall travel can thus be between about 30° and 80°. Preferably, the range of the angle of rotation is about ±30 degrees and the overall travel is thus about 60 degrees. However, angles of rotation of up to about ±90° are entirely feasible.

The frequency of alternating rotary movement 196 of bristle head 150 can be between about 50 Hz and about 80 Hz. Preferably, the frequency should be about 63 Hz.

As mentioned, when electric toothbrush 100 is in an operating mode, motor shaft 160 of the electric motor rotates in continuous fashion. Due to its eccentric inner race 186, the entire ball bearing 184 vibrates. In other words, inner race 186 serves to generate the vibration. Cantilever 126, pressed against outer race 188 of the ball bearing by leaf spring 194, transfers this vibration to rocker arm 120. As a result, the rocker arm is set into a vibrating swivel motion around axis 140.

As explained above, brush attachment 104, when mounted, constitutes an integral part of the rocker arm 120. Consequently, the brush attachment, along with bristle head 150, is set into a vibrating swivel motion around axis 140. Since axis 140 is oriented approximately at a right angle to pin 152, the bristle head follows a reciprocating stroke movement 198, in a direction essentially parallel with pin 152. This essentially parallel alignment of the bristles 106 and pin 152 ultimately causes the bristles to deliver a poking action in the direction in which the bristles extend.

The travel of reciprocating stroke 198 of bristle head 150, and thus the poking action of bristles 106, can be over a distance in the range between about ±0.02 mm and about ±0.2 mm; the total travel thus being about 0.04 mm to about 0.4 mm. Preferably, this travel movement of stroke 198 in either direction is about ±0.05 mm, and the overall travel is thus about 0.1 mm.

The frequency of the back-and-forth movement, i.e., reciprocating stroke 198 of bristle head 150, and thus of the poking action of bristles 106, can be between about 130 Hz and about 200 Hz, and is preferably about 164 Hz. The frequency of the reciprocating stroke movement is thus higher, and preferably substantially higher, than the frequency of alternating rotary movement 196.

The rotary movement (196) and the stroke movement (198) of bristle head 150 are both generated by electric motor 114. The frequency of reciprocating stroke 198 of the bristle head corresponds directly to the rotational speed of the electric motor. The frequency of alternating rotary movement 196 of the bristle head, however, is determined by the rotational speed of the electric motor as modulated by quadrilateral link 158. Accordingly, the frequency ratio of the alternating rotary movement to that of the reciprocating stroke movement is a finite value, or a periodic fraction, or a non-periodic fraction.

When electric toothbrush 100 is switched on for the purpose of cleaning the user's teeth, the user applies bristles 106 to his dental surfaces. As a result, a certain force acts on the bristles, which is indicated in FIG. 11 by arrow 200.

As has been explained, cantilever 126 of rocker arm 120 is pressed against outer race 188 of ball bearing 184 by leaf spring 194. The cantilever also pushes against that side of the ball bearing on which bristle head 150 is located. Now if the user applies a force 200 to the bristles of the bristle head which exceeds a certain level, the result will be that cantilever 126 is lifted off of outer race 188 of the ball bearing, against the spring action of leaf spring 194. The vibration generated by the ball bearing is thus no longer transferred to the rocker arm, nor, consequently, to the bristle head and the bristles. In other words, if and when force 200 exceeds that certain level, the retraction of cantilever 126 away from ball bearing 184 will turn off the reciprocating stroke movement 198 of the bristle head, and with it the poking action of the bristles.

The specific pressure level of force 200 at which cantilever 126 is lifted off of ball bearing 184 can be predetermined by the selection of the appropriate elasticity constant of leaf spring 194. The greater the elasticity constant, the stronger the force with which the leaf spring presses the cantilever against the ball bearing, and the greater the amount of force needed to lift the cantilever off of the ball bearing.

The specific level of force 200 may be in the range of about 1.5 Newton to about 4.0 Newton, and is preferably held at about 2.0 Newton.

In addition, or as an alternative thereto, it is possible to provide mechanical devices which serve to lift cantilever 126 of rocker arm 120 off of outer race 188 of ball bearing 184. Devices of this type allow for the switching-off of the reciprocating stroke movement 198 of bristle head 150, and thus of the poking action of the bristles, independent of the force 200 at which the user presses the bristles against his dental surfaces. Such a device may be, for instance, a lever that can be actuated by the user, and which lifts cantilever 126 off of the ball bearing. This gives the user the option of activating and deactivating the reciprocating stroke movement of the bristle head at will.

Figure 14:
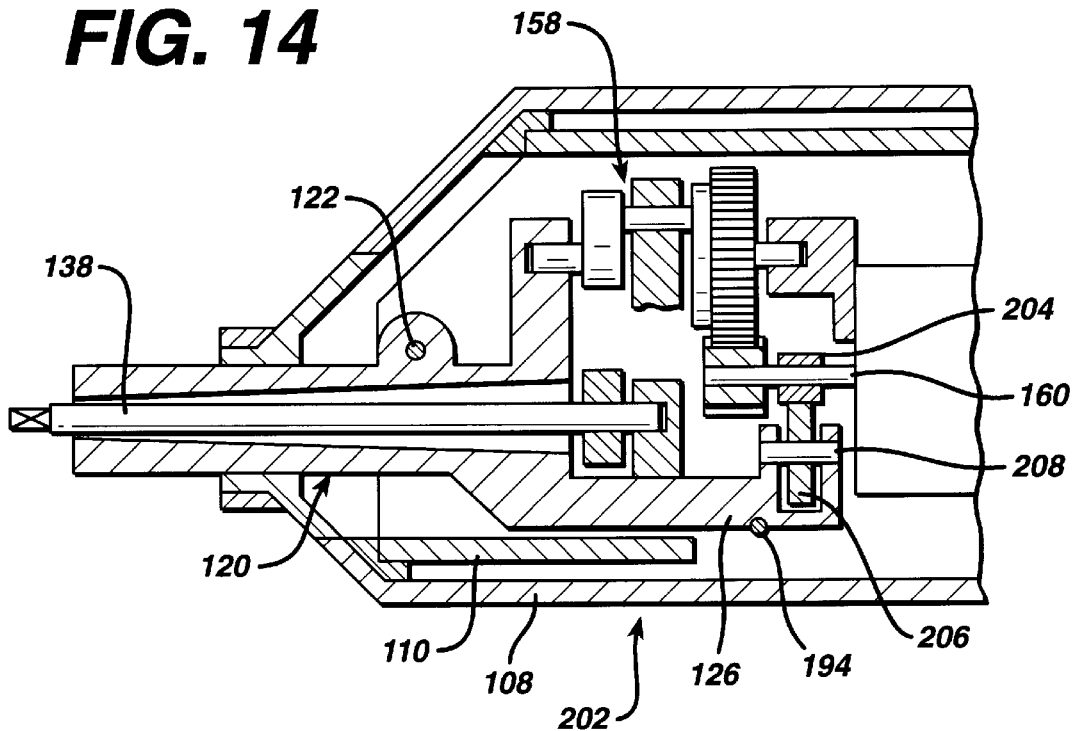
FIG. 14 is a schematic illustration, along a longitudinal section, of a second design example of an electric toothbrush.

FIG. 14 illustrates a second design example of an electric toothbrush 202, which in its configuration and function is very similar to electric toothbrush 100 of FIGS. 11 through 13. The difference lies in the approach to generating the vibration of rocker arm 120, which in the electric toothbrush of FIG. 14 is not brought about by a ball bearing with an eccentric inner race. Therefore, the following only describes the components which differ from those in electric toothbrush 100. Identical components bear identical reference numbers.

In electric toothbrush 202 shown in FIG. 14, the vibration is generated by means of an eccentric element 204 which is mounted in fixed position on motor shaft 160 of electric motor 114. The eccentric element may be in the form of a wheel or similar element, which is either seated in off-center fashion, or displays an eccentric circumference. The free end of cantilever 126 of rocker arm 120 is provided with a rotating roller 206, which is mounted on a spindle 208 that extends approximately parallel with motor shaft 160. Roller 206 bears on the eccentric element 204 and, as the motor shaft rotates, rolls with its circumference along the circumference of the eccentric element. As a result, when electric toothbrush 202 is in operating mode, rocker arm 120 is vibrated by eccentric element 204, and the revolving roller 206 on it. This vibration, as explained above, is transferred to bristle head 150 where it generates reciprocating stroke movement 198.

As an alternative to roller 206, a guide shoe may be provided which slides along the circumference of the eccentric element 204.

Another possible approach involves the use of ball bearing 184 as shown in FIGS. 11 through 13, with roller 206 of FIG. 14 in contact with, and rolling along the circumference of, the outer race of the ball bearing.

As another additional or alternative approach, outer race 188 of ball bearing 184 is not concentric as shown in FIGS. 11 through 13, but is instead eccentric. When combined with roller 206, this will generate a vibration which is a composite of the vibration derived from eccentric inner race 186, and the vibration generated by the eccentric outer race.

Another possible alternative is to use an eccentric wheel in lieu of roller 206, mounted on cantilever 126 as shown in FIG. 14. To that effect, the wheel is either mounted off-center or has an eccentric circumference. In this case it is not necessary to equip the wheel with any other component that would be mounted on motor shaft 160 of electric motor 114. The eccentric wheel bears directly on the motor shaft and revolves as the motor shaft rotates. Due to the eccentric shape of the wheel, rocker arm 120 is set in a vibratory motion which, in turn, produces the reciprocating stroke motion 198 of bristle head 150, and with it the poking action of the bristles.

Figure 15:
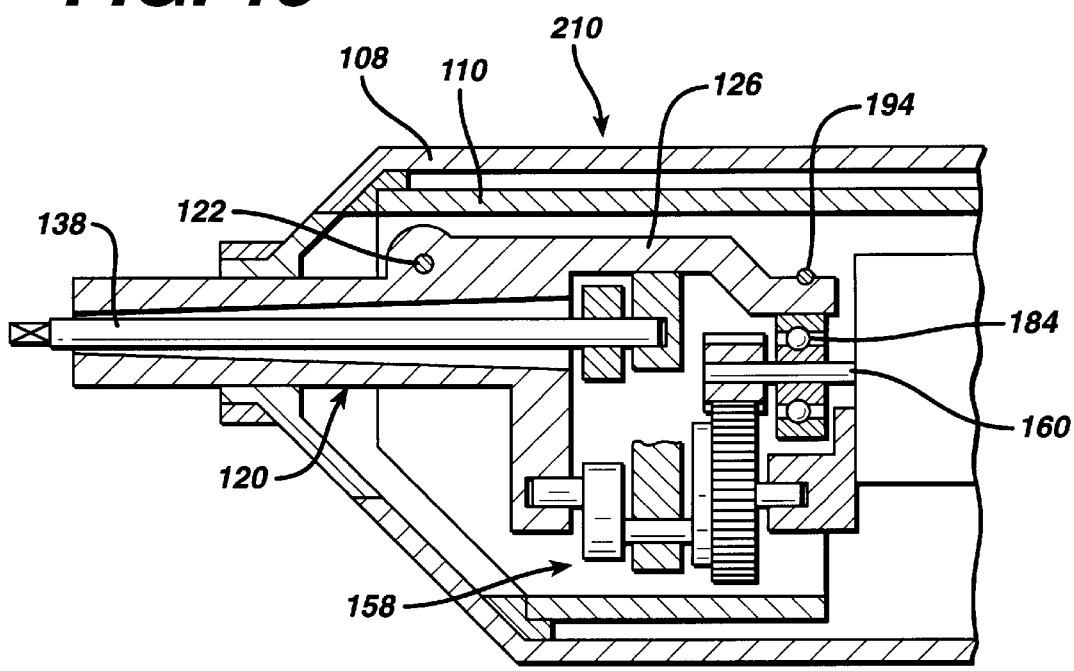
FIG. 15 is a schematic illustration, along a longitudinal section, of a third design example of an electric toothbrush.

FIG. 15 illustrates a third design example of an electric toothbrush 210, which in terms of its structural concept and function is very similar to electric toothbrush 100 of FIGS. 11 through 13. The only difference is the location of cantilever 126 of rocker arm 120, which in electric toothbrush 210 of FIG. 15 is not on the same side of shaft 138 as bristle head 150. Therefore, the following describes only the components which differ from those in electric toothbrush 100. Identical components bear identical reference numbers.

In electric toothbrush 210 shown in FIG. 15, cantilever 126 of rocker arm 120 bears on outer race 188 of ball bearing 184 on that side which is located opposite bristle head 150. As a result, the cantilever will always be in a state where leaf spring 194 presses it against the ball bearing. Even force 200 applied to bristles 106 will not lift the cantilever off of the ball bearing. In this case, leaf spring 194 only serves to provide initial spring tension. The reciprocating stroke movement 198 of bristle head 150, and consequently the poking action of the bristles, remain in effect regardless of any force 200.

For space reasons it is necessary in the case of electric toothbrush 210 of FIG. 15 to position quadrilateral link 158 on the other side of rocker arm 120, relative to electric toothbrush 100 of FIGS. 11 through 13.

As another possible alternative, the vibration, and with it the reciprocating stroke movement 198 of the bristle head, are not generated by an electric motor 114 as provided for in the figures, but by an independent drive system. As a result, the frequency of the reciprocating stroke movement 198 of the bristle head, and the frequency of the poking action of the bristles, will be independent of the frequency of the alternating rotary movement 196 of the bristle head. The separate drive system for stroke movement 198 may, for instance, be a second electric motor, or an electromagnetic oscillator, or a piezoelectric actuator.

What is claimed is:
1. An oral brush comprising:
  a body including
    a) an elongated handle having a longitudinal extent and a first end, and
    b) a head positioned at said first end, said head being constructed for insertion into an oral cavity of a human;
  a plurality of non-crimped bristles extending from said head at an angle to said longitudinal extent of said elongated handle; and
  a plurality of crimped bristles extending from said head, said crimped bristles defining a regularly repeating wave form or combination of wave forms, each crimped bristle having substantially the same crimp geometry as each of the other crimped bristles and a diameter of from about 0.006 inch to 0.020 inch,
  said brush being constructed to cleanse the oral cavity.
2. The oral brush of claim 1 wherein the crimp of the bristles is substantially sinusoidal.
3. The oral brush of claim 1 wherein the crimp has an amplitude of from about 0.01 to 1.0 millimeter.
4. The oral brush of claim 1 wherein the crimp has a frequency of from about 0.5 to 8 crimps per centimeter.
5. The oral brush of claim 1 wherein the crimp of at least a portion of the bristles is surface crimp.
6. The oral brush of claim 5 wherein said surface crimp has a width of from about 0.05 to 2.0 millimeter.
7. The oral brush of claim 5 wherein said surface crimp has a ratio of depth of crimp to bristle diameter of from about 0.01 to 0.20.
8. The oral brush of claim 1 wherein the crimp of neighboring bristles is in-phase.
9. The oral brush of claim 1 wherein the crimp of neighboring bristles is out-of-phase.
10. The oral brush of claim 9 wherein the out-of-phase configuration is substantially random.
11. The oral brush of claim 1 wherein the bristles comprise filaments having a diameter of from about 0.006 to 0.015 inch.
12. The oral brush of claim 1, wherein the bristles result in a brush having a stiffness grade (ISO 8627) of no greater than 7 centinewtons per square millimeter.
13. The oral brush of claim 1 wherein the bristles result in a brush having a stiffness grade (ISO 8627) of from about 2 to 7 centinewtons per square millimeter.
14. The oral brush of claim 1 wherein said non-crimped bristles are mounted along a perimeter region of said head and said crimped bristles are mounted on a central region of said head.
15. The oral brush of claim 14 wherein said crimped bristles have a diameter of about 0.006 inch.
16. The oral brush of claim 15 wherein said crimped bristles are mounted in tuft holes and each said tuft hole contains from 40 to 56 crimped bristles.
17. The oral brush of claim 14 wherein said non-crimped bristles are mounted along a perimeter of the head and said crimped bristles are mounted on two spaced symmetrical central regions of said body.
18. The oral brush of claim 17 wherein said spaced, symmetrical central regions of said head are semi-circular.

19. The oral brush of claim 1 wherein said non-crimped bristles are mounted on a central region of said head and said crimped bristles are mounted along a perimeter region of said head.

20. The oral brush of claim 1 wherein said crimped bristles contain a dye that is releasable from the crimped bristles during use to indicate the wear of the brush-head.

21. The oral brush of claim 1 comprising an electric toothbrush.

22. The oral brush of claim 21 wherein said electric toothbrush includes a brush head selected from the group consisting of vibrating, oscillating, and rotating brush heads.

23. The oral brush of claim 21 wherein said electric toothbrush comprises a brush head, said plurality of crimped bristles being arranged in a tuft extending from said brush head.

24. The oral brush of claim 23 wherein said brush head comprises tufts of crimped bristles and tufts of straight bristles.

25. The oral brush of claim 24 wherein said tufts of crimped bristles are arranged in an inner region of the brush head, surrounded by said tufts of straight bristles arranged in an outer region of the brush head.

26. The oral brush of claim 25 wherein at least some of said tufts of straight bristles extend from said brush head beyond said tufts of crimped bristles.

27. The oral brush of claim 25 wherein said tufts of straight bristles each have at least about 8 percent more bristles than each of said tufts of crimped bristles.

28. The oral brush of claim 23 wherein said tuft of crimped bristles has a base end at said head and a distal end, the tuft of crimped bristles being splayed, at rest, such that it occupies a substantially wider area at its distal end than at its base end.

29. The oral brush of claim 21 wherein said crimped bristles have a diameter of about 0.006 inch.

30. The oral brush of claim 23 adapted to rotate said brush head about a rotational axis substantially parallel to the longitudinal axis of said tuft, and to cyclically move the brush head in the direction of said rotational axis.

31. The oral brush of claim 30 wherein said brush head comprises
 tufts of crimped bristles arranged in an inner region of the brush head, and
 tufts of straight bristles arranged about the periphery of said inner region, at least two of said tufts of straight bristles extending beyond the distal ends of said tufts of crimped bristles and being separated by a distance of about 10 millimeters.

32. An oral brush comprising:
a) body including
 a an elongated handle having a longitudinal extent and a first end, and
b) a head positioned at said first end, said head being constructed for insertion into an oral cavity of a human;
a plurality of crimped bristles extending from said head, said crimped bristles defining a regularly repeating wave form or combination of wave forms, each crimped bristle having a diameter of from about 0.006 inch to 0.020 inch; and
a plurality of non-crimped bristles extending from said head at an angle to said longitudinal extent of said handle.

33. The oral brush of claim 32, wherein the crimp has an amplitude of from about 0.01 to 1.0 millimeter.

34. The oral brush of claim 32 wherein the crimp has a frequency of from about 0.5 to 8 crimps per centimeter.

35. The oral brush of claim 32 wherein the crimp of atleast a portion of the bristles is surface crimp.

36. The oral brush of claim 35 wherein said surface crimp has a width of from about 0.05 to 2.0 millimeter.

37. The oral brush of claim 35 wherein said surface crimp has a ratio of depth of crimp to bristle diameter of from about 0.01 to 0.20.

38. The oral brush of claim 32 wherein the crimp of neighboring bristles is out-of-phase.

39. The oral brush of claim 32 wherein the bristles result in a brush having a stiffness grade (ISO 8627) of now greater tham 7 centinewtons per square millimeter.

40. The oral brush of claim 32 wherein the bristles result in a brush having a stiffness grade (ISO8627) of up to 9 centinewtons per square millimeter.

41. The oral brush of claim 32 wherein the bristles result in a brush having a stiffness grade (ISO 8627) of from aabout 2 to 7 centinewtons per square millimeter.

42. The oral brush of claim 32 where said non-crimped bristles are mounted along a perimeter region of said head and said crimped bristles are mounted on a central region of said head.

43. The oral brush of claim 32 wherein said non-crimped bristles are mounted on a central region of said head and said crimped bristles are mounted along a perimeter region of said head.

44. The oral brush of claim 42 wherein said non-crimped bristles are mounted along a perimeter of the head and said crimped bristles are mounted on two spaced symmetrical central regions of said body.

45. The oral brush of claim 44 wherein said spaced, symmetrical central regions of said head are semi-circular.

46. An oral brush comprising:
 a body including a head constructed to be inserted into an oral cavity;
 a plurality of crimped bristles extending from said head, said crimped bristles defining a regularly repeating wave form or combination of wave forms, each crimped bristle having substantially the same crimp geometry as each of the other crimped bristles, said crimped bristles being mounted along perimeter region of said head; and
 a plurality of non-crimped bristles mounted on a central region of said head,
 said brush constructed to cleanse the oral cavity.

47. The oral brush of claim 46 wherein said crimped bristles have a diameter of about 0.006 inch.

48. The oral brush of claim 47 wherein said crimped bristles are mounted in tuft holes and each said tuft hole contains from about 40 to 56 crimped filaments.

49. The oral brush of claim 46 wherein said body includes an elongated handle having a longitudinal extent and a first end, and said head is positioned at said first end.

50. An oral brush comprising:
 a body including a head constructed to be inserted into an oral cavity;
 a plurality of crimped bristles extending from said head, said crmped bristles defining a regularly repeating wave form or combination of wave forms, each crimped bristle having substantially the same crimp geometry as each of the other crimped bristles, said crimped bristles being mounted on two, spaced symmetrical, semi-circular central regions of said head; and a plurality of non-crimped bristles mounted along a perimeter region of said head, said brush constructed to cleanse the oral cavity.

51. The oral brush claim 50 wherein said body includes an elongated handle having a longitudinal extent and a first end, and said head is positioned at said first end.

52. An oral brush comprising:

an electric toothbrush that comprises a head constructed to be inserted into an oral cavity;

a plurality of crimped bristles arranged in tufts extending from said head, said crimped bristles defining a regularly repeating wave form or combination of wave forms, each crimped bristle having substantially the same crimp geometry as each of the other crimped bristles; and tufts of straight bristles extending from said head, said brush constructed to cleanse the oral cavity.

53. The oral brush of claim 52 wherei said tufts of crimped bristles are arranged in an inner region of said brush head surrounded by said tufts of straight bristles arranged in an outer region of said brush head.

54. The oral brush of claim 53 wherein at least some of said tufts of straigt bristles extend from said brush head beyond said tufts of crimped bristles.

55. The oral brush of claim 53 wherein said tufts of straight bristles each have at least about 8 percent more bristles than each of said tufts of cirmped bristles.

56. The oral brush of claim 52 further including elongated handle having a longitudinal extent and a first end, and said head is poisitoned at said first end.

57. Theoral brush of claim 52 wherein said straight bristles are mounted on a central region of said head and said crimped bristles are mounted along a perimeter region of said head.

58. The oral brush of claim 52 wherein said straght bristles are mounted along a perimeter of the head and said crimpted bristles are mounted on two spaced symmetrical central regions of said head.

59. The oral brush of claim 58 wherein said spaced, symmetrical central regions of said head are semi-circular.

60. An oral brush comprising:

a body including a head constructed to be inserted into an oral cavity;

a plurality of crimped bristles extending from said head, said crimped bristles defining a regularly repeating wave form or combination of wave forms, each crimped bristle having substantially the same crimpe geometry as each of the other crimped bristles, said plurality of crimped bristles being arranged in a tuft extending from said head, said tuft of crimped bristles being arranged in an inner region of the head; and tufts of straight bristles arranged about the periphery of said inner region, at least two of said tufts of straight bristles extending beyond the distal ends of said tuft of crimped bristles and being separated by a distance of about 10 millimeters, said oral brush comprising an electric toothbrush adapted to rotate said head about a rotational axis substantially parallel to the longitudinal axis of said tuft, and to cyclically move the head in the directionof said rotatinal axis, said oral brush constructed to cleasnse the oral cavity.

61. The oral brush of claim 60 wherein said body includes an elongated handle having a longitudinal extent and a first end, and said head is positioned at said first end.

62. An oral brush comprising:

a body including a) an elongated handle having a longitudinal extent and a first end, and b) a head positioned at said first end, said head being constructed for insertion into an oral cavity of a human;

a plurality of non-crimped bristles extending from said head at an angle to said longitudinal extent of said elongated handle; and a plurality of crimped bristles extending from said head, said crimped bristles defining a regularly repeating wave form or combination of wave forms, said crimped bristles having a stiffness grade that is about 20% lower than the stiffness grade of straght bristles of the same material having the same diameter, said brush being constructed to cleanse the oral cavity.

* * * * *